United States Patent [19]
Beeley et al.

[11] Patent Number: 5,519,006
[45] Date of Patent: May 21, 1996

[54] PHOSPHONATED ARYLETHANOLAMINE COMPOUNDS WITH ANTI-HYPERGLYCEMIC AND/OR ANTI-OBESITY ACTIVITY

[75] Inventors: Lee J. Beeley, Dorking; John M. Berge, Merstham; Richard L. Jarvest, Surbiton, all of England

[73] Assignee: SmithKline Beecham plc, Brentford, England

[21] Appl. No.: 374,745

[22] Filed: Mar. 30, 1995

[30] Foreign Application Priority Data

Jul. 25, 1992 [GB] United Kingdom ............... 9215844

[51] Int. Cl.$^6$ ............... A61K 31/66; C07F 9/38; C07F 9/40
[52] U.S. Cl. ............... 514/114; 514/89; 514/91; 514/110; 514/112; 514/119; 546/22; 548/413; 558/83; 558/167; 558/174; 558/179; 558/187; 562/11; 562/15
[58] Field of Search ............... 514/114; 558/179, 558/187; 562/11

[56] References Cited

FOREIGN PATENT DOCUMENTS

| | | |
|---|---|---|
| 0102213 | 8/1983 | European Pat. Off. . |
| 0262785 | 8/1987 | European Pat. Off. . |
| 0455006A2 | 4/1991 | European Pat. Off. . |

*Primary Examiner*—Johann Richter
*Assistant Examiner*—Michael G. Ambrose
*Attorney, Agent, or Firm*—Charles M. Kinzig; Stephen Venetianer; Edward T. Lentz

[57] ABSTRACT

A compound of formula (I) or a pharmaceutically acceptable salt, ester or amide thereof, or a pharmaceutically acceptable solvate thereof, wherein $R^0$ represents a substituted or unsubstituted aryl group; $R^1$ represents hydrogen or an alkyl group; $R^2$ represents a moiety of formula (a) wherein $R^4$ and $R^5$ each independently represent hydrogen, alkyl, hydroxyalkyl, cycloalkyl or $R^4$ together with $R^5$ represents $(CH_2)_n$ wherein n is 2, 3 or 4; T represents hydrogen, nitrile or a group —$CO.R^s$ wherein $R^s$ represents hydroxy, alkoxy or a group —$NR'R''$ wherein $R'$ and $R''$ independently represent hydrogen, alkyl or $R'$ and $R''$ together with the nitrogen to which they are attached represent a saturated heterocyclic group; and $R^3$ represents hydrogen, halogen, alkyl or alkoxy; a process for the preparation of such a compound, a pharmaceutical composition comprising such a compound and the use of such a compound in medicine.

16 Claims, No Drawings

PHOSPHONATED ARYLETHANOLAMINE COMPOUNDS WITH ANTI-HYPERGLYCEMIC AND/OR ANTI-OBESITY ACTIVITY

This application was filed under 35 U.S.C. 371 and is a continuation of PCT International Application No. PCT/GB93/01554, filed on Jul. 22, 1993.

This invention relates to novel compounds, to a process for preparing such compounds, to pharmaceutical compositions containing such compounds and to the use of such compounds and compositions in medicine and agriculture.

European patent application, publication number 0455006 discloses certain arylethanolamine derivatives which are stated to possess anti-diabetic and/or anti-hyperglycaemic and/or anti-obesity activity.

It has been discovered that a series of novel phosphonated arylethanolamine derivatives have good β-adrenoreceptor agonist activity and in particular show good selectivity for $β_3$-adrenoreceptors versus $β_1$- or $β_2$-adrenoreceptors. These compounds are therefore indicated to have good anti-hyperglycaemic and/or anti-obesity activity coupled with especially good selectivity from cardiac and tremorigenic side effects.

They are also indicated to have potential in the treatment of gastrointestinal dims such as irritable bowel syndrome.

These compounds also have potential as grog promoters for livestock and for decreasing birth mortality rate and increasing the post-natal survival rate in livestock. These compounds may also be of use in increasing the high-density-lipoprotein (HDL) cholesterol concentration and decreasing the triglyceride concentration in human blood serum and are therefore of potential use in the treatment and/or prophylaxis of atherosclerosis. They are also indicated to be useful for the treatment of hyperinsulinaemia.

Accordingly the present invention provides a compound of formula (I):

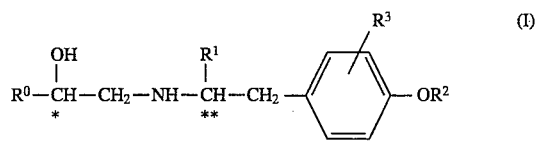

or a pharmaceutically acceptable salt, ester or amide thereof, or a pharmaceutically acceptable solvate thereof, wherein, $R^o$ represents a substituted or unsubstituted aryl group;

$R^1$ represents hydrogen or an alkyl group;

$R^2$ represents a moiety of formula (a):

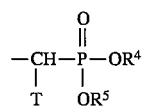

wherein $R^4$ and $R^5$ each independently represent hydrogen, alkyl, hydroxyalkyl, cycloalkyl or $R^4$ together with $R^5$ represents $(CH_2)_n$ wherein n is 2, 3 or 4;

T represents hydrogen, nitrile or a group —$CO.R^s$ wherein $R^s$ represents hydroxy, alkoxy or a group —$NR'R''$ wherein $R'$ and $R''$ independently represent hydrogen, alkyl or $R'$ and $R''$ together with the nitrogen to which they are attached represent a saturated heterocyclic group; and $R^3$ represents hydrogen, halogen, alkyl or alkoxy.

Suitably, $R^o$ represents a phenyl group optionally substituted with halogen or a hydroxy, examples include chlorophenyl, especially 3-chlorophenyl, and hydroxyphenyl, especially 3,4-bis-hydroxyphenyl.

Suitably, $R^1$ is an alkyl group.

When $R^1$ is alkyl, it is favourably a $C_{1-6}$ alkyl group, especially a methyl group.

Suitably, $R^4$ and $R^5$ each independently represent alkyl, for example ethyl propyl, or butyl.

Preferably, $R^4$ is alkyl, for example ethyl, propyl or butyl, especially ethyl, and $R^5$ is hydrogen.

Suitably, $R^3$ represents hydrogen.

Suitably, T represents hydrogen or a group —$CO.R^s$ wherein $R^s$ is hydroxy or alkoxy.

Preferably, T represents hydrogen.

The compounds of formula (I) have one or two asymmetric carbon atoms, marked with an asterisk (*) or two asterisks (**) in the formula. These compounds may therefore exist in up to four stereoisomeric forms. The present invention encompasses all stereoisomers of the compounds of the general formula (I) whether free from other isomers, or admixed with other isomers in any proportion, such as mixtures of diastereoisomers and racemic mixtures of enantiomers.

Preferably, the asymmetric carbon atom indicated by a single asterisk (*) is in the R-configuration.

Preferably, the asymmetric carbon atom indicated by two asterisks (**) is in the R-configuration.

One suitable form of a compound of formula (I) is a diastereomeric mixture of the RR and SS enantiomers.

One preferred form of a compound of formula (I) is the RR enantiomer.

The term 'alkyl' when used alone or when forming part of other groups (such as the 'alkoxy' group) includes straight- or branched-chain alkyl groups containing 1 to 12 carbon atoms, suitably 1 to 6 carbon atoms, examples include methyl, ethyl, n-propyl, isopropyl, n-butyl, isobutyl or tert-butyl group.

The term 'cycloalkyl' includes $C_{3-8}$ cycloalkyl groups, especially $C_5$ or $C_6$ cycloalkyl groups.

When used herein the term "halogen" refers to fluorine, chlorine, bromine and iodine, preferably chlorine.

When used herein the term 'aryl' includes phenyl and naphthyl optionally substituted with up to five, preferably up to three, groups selected from halogen, alkyl, phenyl, alkoxy, haloalkyl, hydroxyalkyl, hydroxy, amino, nitro, carboxy and pharmaceutically acceptable salts, esters and amides thereof, alkoxycarbonylalkyl, alkylcarbonyloxy and alkylcarbonyl groups.

A preferred aryl group is a substituted or unsubstituted phenyl group.

Preferred optional substituents for the aryl group include up to three substituents selected from halogen, hydroxy, alkoxy, hydroxyalkyl and amino.

Suitable pharmaceutically acceptable esters of carboxyl groups include alkyl esters, especially $C_{1-6}$ alkyl esters such as methyl.

Suitable pharmaceutically acceptable amides are those of formula —$CONR^xR^y$ wherein $R^x$ and $R^y$ each independently represent hydrogen, alkyl or alkoxyalkyl.

Suitable pharmaceutically acceptable salts include acid addition salts, salts of carboxy groups and salts of phosphonic acid groups.

Suitable pharmaceutically acceptable acid addition salts include salts with inorganic acids such, for example, as hydrochloric acid, hydrobromic acid, orthophosphoric acid or sulphuric acid, or with organic acids such, for example, as methanesulphonic acid, toluenesulphonic acid, acetic acid, propionic acid, lactic acid, citric acid, fumaric acid, malic acid, succinic acid, salicylic acid, maleic acid or acetylsalicylic acid.

Suitable pharmaceutically acceptable salts of carboxy groups or phosphonic acid groups include metal salts, such as for example aluminium, alkali metal salts such as sodium or potassium, alkaline earth metal salts such as calcium or magnesium and ammonium or substituted ammonium salts, for example those with $C_{1-6}$ alkylamines such as methylamine, hydroxy-$C_{1-6}$ alkylamines such as 2-hydroxyethylamine, his-(2- hydroxyethyl)-amine or tri-(2-hydroxyethyl)-amine, cycloalkylamines such as bicyclohexylamine, or with procaine, dibenzylpiperidine, N-benzyl-β-phenethylamine, deehydroabietylamine, N,N'-bisdehydroabietylamine, glucamine, N-methylglucamine or bases of the pyridine type such as pyridine, collidine or quinoline.

Suitable pharmaceutically acceptable solvates are conventional solvates, preferably hydrates.

The invention also provides a process for the preparation of a compound of formula (I), or a pharmaceutically acceptable salt, ester or amide thereof or a pharmaceutically acceptable solvate thereof, which process comprises reducing a compound of formula (II):

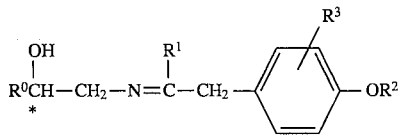

wherein $R^o$, $R^1$, $R^2$ and $R^3$ are as defined in relation to formula (I), and thereafter, if necessary, carrying out one or more of the following optional steps:
(i) converting one compound of formula (I) to another compound of formula (I); and
(ii) preparing a pharmaceutically acceptable salt, ester or amide thereof of a compound of formula (I) or a pharmaceutically acceptable solvate thereof.

The reduction of the compound of formula (II) may be carried out using any suitable reduction procedure, for example by using catalytic reduction in the presence of hydrogen.

Suitable catalysts include platinum oxide or 10% palladium on charcaol.

Suitable reduction conditions include using an alkanolic solvent such as methanol, at any temperature providing a convenient rate of formation of the required product, for example when using the platinum catalyst the reaction may conveniently be carried out at ambient temperature or when using the palladium catalyst the reaction may be carried out at a medium temperature such as 50° C., under a pressure of 1–5 atmospheres of hydrogen.

The compound of formula (II) may be prepared by reacting a compound of formula (III):

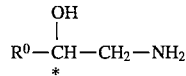

wherein $R^o$ is as defined in relation to formula (I) with a compound of formula (IV):

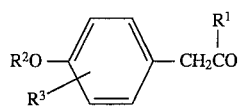

wherein $R^2$ and $R^3$ are as defined in relation to formula (I).

The reaction between compounds of formulae (III) and (IV) may be carried out under conventional amination conditions, for example in a solvent such as methanol or toluene.

Conveniently, the compound of formula (II) is prepared in-situ by reacting a compound of the above defined formula (III) with a compound of the above defined formula (IV) under reductive amination conditions.

Suitable reductive amination conditions include reacting the compounds of formula (III) and (IV) in an alkanolic solvent, such as methanol, in the presence of a suitable reduction catalyst.

Suitable reduction catalysts and reaction conditions are as described above for the reduction of the compound of formula (II).

A compound of formula (IV) may be prepared by reducing a compound of formula (V):

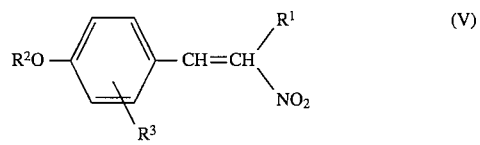

wherein $R^1$, $R^2$ and $R^3$ are as defined in relation to formula (I).

The reduction of the compound of formula (V) may conveniently be carried out using iron powder in the presence of acetic acid in an aqueous solvent such as aqueous methanol, at any temperature providing a suitable rate of formation of the required product, generally at an elevated temperature and conveniently at the reflux temperature of the solvent.

A compound of formula (V) may be prepared by reacting a compound of formula (VI):

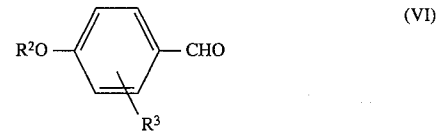

wherein, $R^2$ and $R^3$ are as defined in relation to formula (I), with nitroalkane.

Generally, the carbon atom of the —CHO group of compound of formula (VI) is in an activated form, a suitable activated form being provided by forming an imine of the said carbonyl group: The imine may be prepared by reacting the compound of formula (VI) with an amine, suitably a primary alkyl amine such as n-butylamine. The reaction of the compound of formula (VI) and the amine may be carded out in any suitable solvent, such as toluene, at any temperature providing a suitable rate of formation of the required product, generally at an elevated temperature such as the reflux temperature of the solvent; and preferably in the presence of a catalytic amount of toluenesulphonic acid.

The reaction between the compound of formula (VI), and when it is in the form of an imine, and nitroalkane may be carried out in glacial acetic acid, preferably in the presence of an ammonium acetate catalyst, generally at an elevated temperature such as in the range of from 60° C. to 120° C., for example 100° C.

A compound of formula (VI), wherein T is hydrogen, may be prepared from a compound of formula (VII):

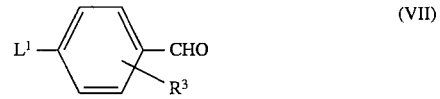

wherein $R^3$ is as defined in relation to formula (I) and $L^1$ is a leaving group or atom, generally a fluorine atom, with an activated form of a compound of formula (VIII):

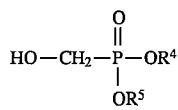

wherein $R^4$ and $R^5$ are as defined in relation to formula (I).

A suitable activated form of a compound of formula (VIII) is an ionic form, such as a salted form, for example an alkali metal salted form.

An activated form of a compound of formula (VIII) may be prepared by use of the appropriate conventional procedure, for example a salted form may be prepared by treating the compound of formula (VIII) with a base such as an alkali metal hydride, for example sodium hydride.

The reaction between the compounds of formulae (VII) and (VIII) may be carried out in any suitable solvent, generally an aprotic solvent such as dimethylformamide or N-methylpyrrolidinone at a low to ambient temperature, for example in the range of from −15° C. to 20° C., such as 5° C.

A compound of formula (IV) may also be prepared by the reaction of a compound of formula (IX):

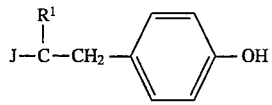

wherein $R^1$, $R^2$ and $R^3$ are as defined in relation to formula (I) and J represents an oxo group or a protected oxo group, for example an ethan-1,2-dioxy group, with a compound of formula (X):

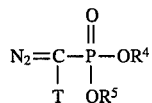

wherein $R^4$, $R^5$ and T are as defined in relation to formula (I) in the presence of a rhodium salt, and thereafter, as required, removing any protecting group.

A suitable rhodium salt is rhodium acetate.

The reaction between the compound of formula (IX) and the compound of formula (X) may be carried out under conventional carbene insertion conditions, in an inert solvent, such as benzene at any temperature providing a convenient rate of formation of the required product, generally at an elevated temperature, such as the reflux temperature of the solven; preferably the reaction is carried out under an inert atmosphere such as nitrogen.

When J is a protected oxo group such as an ethan-1,2-dioxy group it may be removed by treatment with an aqueous acid, such as aqueous hydrochloric acid.

A compound of formula (I) wherein either the *$CH_2$ or the **$CH_2$ carbon is a chiral carbon may be prepared using conventional stereoselective chemistry from appropriate starting materialsis.

One process for the preparation of a compound of formula (I) wherein both the *$CH_2$ and the **$CH_2$ carbon are chiral carbon atoms, or a pharmaceutically acceptable salt, ester or amide thereof or a pharmaceutically acceptable solvate thereof, comprises reacting a compound of formula (XI):

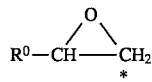

wherein $R^o$ is as defined in relation to formula (I), with a compound of formula (XII):

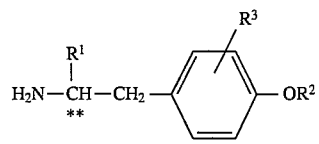

wherein $R^1$, $R^2$ and $R^3$ are as defined in relation to formula (I); and thereafter, if necessary, carrying out one or more of the following optional steps:

(i) convening one compound of formula (I) to another compound of formula (I); and (ii) preparing a pharmaceutically acceptable salt, ester or amide thereof of a compound of formula (I) or a pharmaceutically acceptable solvate thereof.

Suitably, both the *$CH_2$ and the **$CH_2$ carbon atoms have the R stereochemistry.

Suitable reaction conditions for the reaction between the compounds of formulae (XI) and (XII) include using an aprotic solvent such as dimethylsulphoxide, at any temperature providing a convenient rate of formation of the required product, for example at an elevated temperature such as in the range of from 30° C. to 100° C., for example 75° C.: preferably the reaction is carried out under an inert atmosphere such as nitrogen.

A compound of formula (XII) may be prepared by the hydrogenolysis of a compound of formula (XIII):

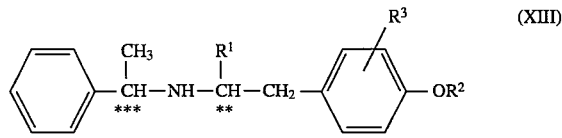

wherein $R^1$, $R^2$ and $R^3$ are as defined in relation to formula (I) and the CH carbon and *CH carbon atoms are chiral carbon atoms.

Suitably, catalytic hydrogenolysis is used, using for example 10% palladium on charcaol in the presence of ammonium formate, suitably in an alkanolic solvent such as methanol, at any temperature providing a convenient rate of formation of the required product, for example at ambient temperature; preferably the reaction is carried out in an inert atmosphere, generably under nitrogen.

The compound of formula (XIII) may be prepared by stereoselective reduction of a compound of formula (XIV):

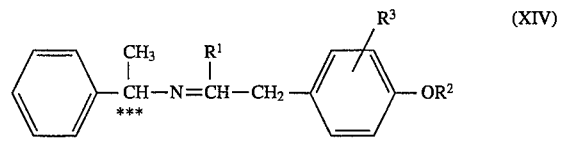

wherein $R^1$, $R^2$ and $R^3$ are as defined in relation to formula (I) and the ***CH carbon is a chiral carbon.

The reduction of the compound of formula (XIV) may be carried out using catalytic reduction in the presence of hydrogen.

A preferred catalyst is platinum oxide.

Suitable reduction conditions include using an alkanol solvent such as methanol or ethanol, at any temperature providing a convenient rate of formation of the required product, conveniently at ambient temperature using a pressure of 1–5 atmospheres of hydrogen.

The compound of formula (XIV) may be prepared by reacting a compound of the above defined formula (IV) with R-α-methylbenzylamine.

The reaction between compounds of formulae (IV) and R-α-methylbenzylamine may be carried out under conventional amination conditions, for example those described above for the reaction between the compounds of formula (III) and (IV). Conveniently, as for the above defined compound of formula (II), the compound of formula (XIV) is prepared in-situ by reacting a compound of the above defined formula (IV) with R-α-methylbenzylamine under reductive amination conditions as described in relation to the compounds of formulae (III) and (IV).

Suitable conversions of one compound of formula (I) into another compound of formula (I) include convening one group $OR^4$ into another group $OR^4$ and/or converting one group $OR^5$ into another group $OR^5$.

Suitable conversions of one group $OR^4$ into another group $OR^4$ include:
(i) converting $OR^4$ as hydroxy into $OR^4$ as alkoxy;
(ii) converting $OR^4$ as alkoxy into $OR^4$ as hydroxy;
(iii) converting $OR^4$ as alkoxy into $OR^4$ as another alkoxy group.

The abovementioned conversion (i) my be carried out under conventional phosphonate alkylation methods, using for example the appropriate alcohol ($R^4OH$) in the presence of hydrogen chloride.

The abovementioned conversion (ii) may be carried out using conventional phosphonate hydrolysis methods, for example by treating the appropriate compound of formula (I) with an alkaline metal hydroxide, such as sodium or lithium hydroxide. This reaction is especially useful when converting $OR^4$ alkoxy into $OR^4$ as hydroxy while leaving $OR^5$ as alkoxy. Alternatively, and especially when it is required to convert both $OR^4$ and $OR^5$ from alkoxy into hydroxy, acidic hydrolysis may be used using for example hydrochloric acid.

The abovementioned conversion (iii) may be carried out by first converting $OR^4$ as alkoxy into $OR^4$ as hydroxy using the conditions set out in respect of the abovementioned conversion (ii), followed by converting the hydroxy group so formed into another alkoxy group, using the conditions set out in respect of the abovementioned conversion (i).

The abovementioned conversion (iii) is of particular use for preparing compounds of formula (I) wherein $OR^4$ represents methoxy: such compounds are generally prepared from compounds of formula (I) wherein $OR^4$ represents an alkyloxy group other than methoxy (suitably ethoxy) by first hydrolysing the relevant $OR^4$ group (via conversion (ii)) to prepare a compound of formula (I) wherein $OR^4$ represents hydroxy and thereafter methylating (via conversion (i)) to provide the required compound wherein $OR^4$ represents methoxy.

Suitable conversions of one group $OR^5$ into another group $OR^5$ include analogous conversions to those mentioned above in regard to converting one group $OR^4$ into another group $OR^4$.

The protection of any reactive group or atom such as the variables $R^o$, $R^1$, $R^2$ and $R^3$, may be carried out at any appropriate stage in the aforementioned processes.

Suitable protecting groups include those used conventionally in the art for the particular group or atom being protected. For example a keto group may be protected as an ketal.

Protecting groups may be prepared and removed using the appropriate conventional procedure. For example a keto group may be protected as an ketal by reaction with an appropriate alcohol, for example ethan-1,2-diol, in the presence of an acid catalyst, such as 4-toluenesulphonic acid. The said ketal may be removed by use of acidic hydrolysis, for example treatment with hydrochloric acid.

A leaving group or atom is any group or atom that will, under the reaction conditions, cleave from the starting material, thus promoting reaction at a specified site. Suitable examples of such groups unless otehwise specified are halogen atoms, mesyloxy groups and tosyloxy groups.

The compounds of formulae (III) and (VIII) are known compounds or they may be prepared by processes analogous to those used to prepare known compounds, for example the compounds of formula (III) may be prepared according to methods disclosed in J. Org. Chem., 1974, 39, 914; and the compounds of formula (VIII) may be prepared according to methods disclosed in Phosphorus and Sulphur, 1978, 5, 455.

The compounds of formula (IX) are known compounds or they may be prepared by methods analogous to those used to prepare known compounds, for example those methods disclosed in European application, publication number 0052963 and United Kingdom patent number 2084577.

The compounds of formulae (X) are either known commercially available compounds or they may be prepared from such compounds by conventional procedures for example those disclosed in the Chem. Berichte 1968, 101, 3734 and The Chemistry of Phosphorus, (J. Emsley and D. Hall), Published by Harper and Row, London, 1976. For example the compounds wherein T represents —$CO.R'R''$ may be prepared from the commercially available compounds wherein T is carboxyl or an ethyl ester thereof, by conventional amination reactions. The compounds of formula (X) wherein T is a nitrile group are conveniently prepared from α-chloroacetonitrile and $P(OR)_3$ whereto R is alkyl, suitably ethyl, and thereafter interconverting R into $R^4$ and or $R^5$ as required.

The compounds of formula (XI) are known compounds or they may be prepared by methods analogous to those used to prepare known compounds, for example those methods disclosed in European application, publication number 0262785.

The salts, esters, amides and solvates of the compounds mentioned herein may be produced by methods conventional in the art: For example, salts may be prepared by treating a compound of formula (I) with the appropriate acid.

Esters of carboxylic acids may be prepared by conventional esterification procedures, for example alkyl esters may be prepared by treating the required carboxylic acid with the appropriate alkanol, generally under acidic conditions.

Amides may be prepared using conventional amidation procedures, for example amides of formula $CONR^sR^t$ may be prepared by treating the relevant carboxylic acid with an amine of formula $HNR^sR^t$, wherein $R^s$ and $R^t$ are as defined above. Alternatively, a $C_{1-6}$ alkyl ester such as a methyl ester of the acid may be treated with an amine of the above defined formula $HNR^sR^t$ to provide the required amide.

Compounds of formula (I) and pharmaceutically acceptable salt, ester or amide thereofs thereof; or a pharmaceutically acceptable solvate thereof, produced by the above processes, may be recovered by conventional methods.

If required mixtures of isomers of the compounds of the invention may be separated into individual stereoisomers by conventional means, for example by the use of an optically active acid as a resolving agent. Suitable optically active acids which maybe used as resolving agents are described in 'Topics in Stereochemistry', Vol. 6, Wiley Interscience, 1971, Allinger, N. L. and Eliel, W. L. Eds.

Alternatively, any enantiomer of a compound of the invention may be obtained by stereospecific synthesis using optically pure starting materials of known configuration.

The absolute configuration of compounds may be determined by conventional X-ray crystallographic techniques.

As previously indicated, the compounds of the present invention have valuable pharmacological properties:

The present invention accordingly provides a compound of formula (I) or a pharmaceutically acceptable salt, ester or amide thereof thereof, or a pharmaceutically acceptable solvate thereof, for use as an active therapeutic substance.

In one aspect, the present invention provides a compound of formula (I), or a pharmaceutically acceptable salt, ester or amide thereof thereof, or a pharmaceutically acceptable solvate thereof, for use in the treatment of hyperglycaemia in human or non-human animals.

The present invention further provides a compound of formula (I), or pharmaceutically acceptable salt, ester or amide thereof thereof, or a pharmaceutically acceptable solvate thereof, for use in the treatment of obesity in human or non-human animals.

A compound of formula (I), or a pharmaceutically acceptable salt, ester or amide thereof thereof, or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of formula (I), or a pharmaceutically acceptable salt, ester or amide thereof thereof, or a pharmaceutically acceptable solvate thereof, and a pharmaceutically acceptable carrier therefor.

As used herein the term "pharmaceutically acceptable" embraces compounds, compositions and ingredients for both human and veterinary use: for example the term "pharmaceutically acceptable salt" embraces a veterinarily acceptable salt.

The composition may, if desired, be in the form of a pack accompanied by written or printed instructions for use.

Usually the pharmaceutical compositions of the present invention will be adapted for oral administration, although compositions for administration by other mums, such as by injection, are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical careers include, for example, microcrystalline cellulose, starch, sodium starch glycollate, polyvinylpyrrolidone, polyvinylpolypyrrolidone, magnesium stearate or sodium lauryl sulphate.

Most suitably the composition will be formulated in unit dose form. Such unit dose will normally contain an amount of the active ingredient in the range of from 0.1 to 1000 mg, more usually 2–100 mg or 0.1 to 500 mg, and more especially 0.1 to 250 mg.

The present invention further provides a method for treating hyperglycaemia in a human or non-human mammal, which comprises administering an effective, non-toxic, amount of a compound of formula (I), or a pharmaceutically acceptable salt, ester or amide thereof thereof, or a pharmaceutically acceptable solvate thereof, to a hyperglycaemic human or non-human mammal in need thereof.

The present invention further provides a method for treating obesity or for the treatment and/or prophylaxis of atherosclerosis in a human or non-human mammal, which comprises administering an effective, non-toxic, amount of a compound of formula (I), or a pharmaceutically acceptable salt, ester or amide thereof, or a pharmaceutically acceptable solvate thereof, to a human or non-human mammal in need thereof.

Conveniently, the active ingredient may be administered as a pharmaceutical composition hereinbefore defined, and this forms a particular aspect of the present invention.

In treating hyperglycaemic or obese humans the compound of formula (I), or a pharmaceutically acceptable salt, ester or amide thereof; or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 1500 mg.

The treatment regimens for atherosclerosis are generally as described for hyperglycaemia.

In treating non-human mammals, especially dogs, the active ingredient may be adminstered by mouth, usually once or twice a day and in an amount in the range of from about 0.025 mg/kg to 25 mg/kg, for example 0.1 mg/kg to 20 mg/kg.

In a further aspect the present invention also provides a method for increasing weight gain and/or improving the feed utilisation efficiency and/or increasing lean body mass and/or decreasing birth mortality rate and increasing post/natal survival rate; of livestock, which method comprises the administration to livestock of an effective non-toxic amount of a compound of formula (I) or a veterinarily acceptable salt, ester or amide thereof thereof, or a veterinarily acceptable solvate thereof.

Whilst the compounds of formula (I) and the veterinarily acceptable salts thereof or a veterinarily acceptable solvate thereof, may be administered to any livestock in the above-mentioned method, they are particularly suitable for increasing weight gain and/or feed utilisation efficiency and/or lean body mass and/or decreasing birth mortality rate and increasing post-natal survival rate; in poultry, especially turkeys and chickens, cattle pigs and sheep.

In the preceding method the compounds of formula (I) or veterinarily acceptable salt, ester or amide thereof will normally be administered orally although non-oral modes of administration, for example injection or implantation, are also envisaged. Suitably the compounds are administered in the feed-stuff or drinking water provided for the livestock. Conveniently these are administered in the feed-stuff at from $10^{-3}$ ppm–500 ppm of total daily fed intake, more usually 0.01 ppm to 250 ppm, suitably less than 100 ppm.

The particular formulations used will of course depend upon the mode of administration but will be those used conventionally in the mode of administration chosen. For administration in feed-stuff the drugs are conveniently formulated as a premix in association with a suitable carrier.

Accordingly, the present invention also provides a veterinarily acceptable premix formulation comprising a compound of formula (I), or a veterinarily acceptable salt, ester or amide thereof thereof; or a veterinarily acceptable solvate thereof, in association with a veterinarily acceptable career therefore.

Suitable carriers are inert conventional agents such as powdered starch. Other conventional feed-stuff premix carriers may also be employed.

No unacceptable toxicological effects am expected when compounds of the invention are administered in accordance with the present invention.

The following Examples illustrate the invention but do not limit it in any way.

PROCEDURE 1

Diethyl 4-formylphenoxymethylphosphonate

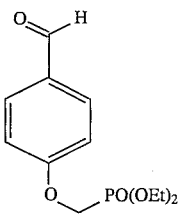

To a suspension of sodium hydride (6.588, of a 60% dispersion in oil, previously washed with hexane)in dimethylformamide (100 ml) was added dropwise diethyl phosphite (21.44 g, 0.155 Mol). The resultant mixture was stirred for 0.5 h at room temperature then treated with paraformaldehyde (4.8 g, 0.16 Mol) in one portion. After stirring for 1.5 h, the mixture was cooled to 5° C. and 4-fluorobenzaldehyde (19.22 g, 0.154 Mol) was added dropwise. After 1.5 h, the mixture was poured into water (500 ml) saturated with ammonium chloride. The organic material was extracted with diethyl ether (3×150 ml), the combined organic phases were washed with water (3×100 ml), dried and evaporated to yield a dark yellow oil. Chromatography on silica gel eluting with 0–25% ethyl acetate in hexane to yield the title compound as a pale yellow oil.

$^1$H-nmr δ(CDCl$_3$), 9.87 (1H, s); 7.85 (2H, d, J=10 Hz); 7.05 (2H, d, J=10 Hz); 4.5–3.9 (6H, complex multiplet); 1.33 (6H, t, J=7.00 Hz).

PROCEDURE 2

Diethyl 4-(2-nitropropenyl)phenoxymethylphosphonate

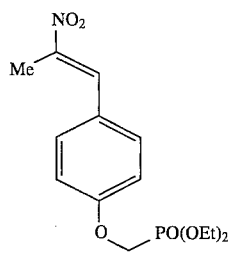

A mixture of diethyl 4-formylphenoxymethylphosphonate (11.0 g, 42.2 mMol), n-butylamine (3.1 g, 42.4mMol) and 4-toluenesulphonic acid (50 mg) dissolved in toluene (75 ml) was heated under reflux for 1.5 h with concomitant removal of water. The reaction mixture was cooled and the solvent evaporated to yield a brown oil (12.1 g). This oil was dissolved in glacial acetic acid (40 ml) containing nitroethane (3.1 ml, 3.2 g, 42.7 mMol) and heated at 100° for 1.5 h. After cooling, the reaction mixture was poured into water (250 ml) and extracted with ethyl acetate (2×150 ml). The combined organic extracts were washed with water (2×100 ml), dried and evaporated to yield a dark yellow oil (13.2 g). Chromatography on silica gel eluting with 0–2% methanol in dichloromethane in gave the title compound as a light yellow oil.

$^1$H-nmr δ(CDCl$_3$), 8.03 (1H, s); 7.42 (2H, d, J=10 Hz); 7.06 (2H, d, J=10 Hz); 4.5–3.9 (6H, complex multiplet); 2.38 (3H, s); 1.38 (6H, t, J=7.0 Hz).

PROCEDURE 3

Diethyl 4-(2-oxopropyl)phenoxymethylphosphonate

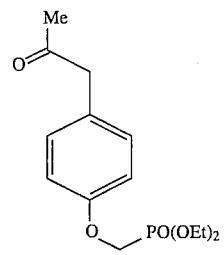

To a mixture of diethyl 4-(2-nitropropenyl)phenoxymethylphosphonate (6.9 g 21.0 mMol) and iron powder (15 g, 267 mMol) in methanol (75 ml) and water (25 ml) under reflux was added acetic acid (50 ml) dropwise. After 3 h the reaction mixture was cooled and filtered through celite, the methanol was evaporated and the residue poured into water/ethyl acetate, filtered through celite and the organic phase separated. The aqueous phase was extracted once with ethyl acetate and the combined organic layers washed with water (2×100 ml), dried and evaporated to yield a dark red oil. Chromatography on silica gel eluting with 0–25% ethyl acetate in hexane gave the title compound as a light yellow oil.

$^1$H-nmr δ(CDCl$_3$), 7.13 (2H, d, J=8.8 Hz); 6.93 (2H, d, J=8.8 Hz); 4.3–4.1 (6H, complex multiplet); 3.65 (2H, s); 2.15 (3H, s); 1.36 (6H, t, J=7.15 Hz).

PROCEDURE 4

(RR)-Diethyl 4-[2-[2-(1-phenylethyl)amino]propyl]phenoxymethylphosphonate

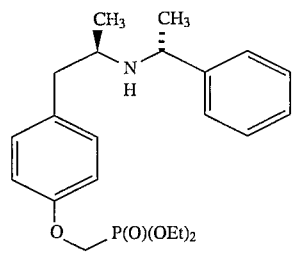

A solution of diethyl 4-(2-oxopropyl)phenoxymethylphosphonate (3.00 g, 10 mMol) and R-α-methylbenzylamine (1.21 g, 10 mMol) dissolved in methanol (50 ml) was hydrogenated in the presence of platinum IV oxide (25 mg) at atmospheric pressure and room temperature. After 16 h the mixture was filtered and the solvent evaporated to yield the crude compound as a light yellow oil. Chromatography over silica gel eluting with dichloromethane containing 3% methanol gave the title compound as a colourless oil.

$^1$H NMR δ(CDCl$_3$), 7.36–7.22 (5H,m); 7.01 (2H,d,J=6.60 Hz); 6.86 (2H,d,J=6.59 Hz); 4.29–4.20 (6H,m); 3.91 (1H, q,J=6.60 Hz); 2.84–2.69 (2H, m); 2.49–2.41 (1 H,m); 1.55 (1H, brs); 1.36 (6H,t,J=7.42 Hz); 1.29 (3H,d,J=6.59 Hz); 0.89 (3H,d,J=6.32 Hz).

PROCEDURE 5

(R)-Diethyl 4-[2-aminopropyl]phenoxymethylphosphonate

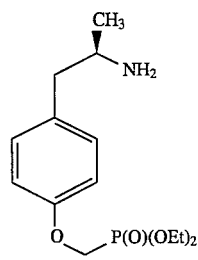

A mixture of (RR)-diethyl 4-[2-[2-(1-phenylethyl)amino] propyl]phenoxymethylphosphonate (2.39 g, 5.9 mMol) ammonium formate (3 g, 47.5 mMol) and 10% palladium on charcoal (300 mg) in methanol (30 ml) was heated at reflux under an atmosphere of nitrogen. After 2 h the mixture was cooled and filtered, the methanol evaporated and the residue partitioned between water (50 ml) and dichloromethane (50 ml). The aqueous layer was extracted once with dichloromethane (50 ml) and the combined organic layers dried and evaporated to yield the title compound as colourless oil.

$^1$H NMR δ(CDCl$_3$), 7.12 (2H,d,J=8.53 Hz); 6.90 (2H,d, J=8.52 Hz); 4.29–4.18 (6H,m); 3.24–3.12 (1H,m); 2.75–2.45 (4H,m); 1.36 (6H,t,J=7.15 Hz); 1.13 (3H,d,J=6.32 Hz).

PROCEDURE 6

(RR)-Diisopropyl 4-[2-[2-(1-phenylethyl)amino]propyl]phenoxymethylphosphonate

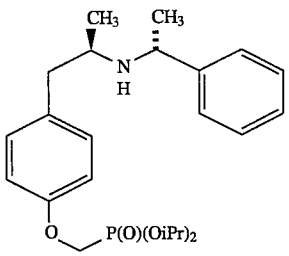

The title compound was obtained from diisopropyl 4-(2-oxopropyl)phenoxymethylphosphonate (3.0 g, 9.1 mMol), R-α-methylbenzylamine (1.1 g, 9.1 mMol) and platinum IV oxide (25 mg) in ethanol (30 ml) by an analogous procedure to that described in Procedure 4 after chromatography over silica gel during with dichloromethane containing 3% methanol.

$^1$H NMR δ(CDCl$_3$), 7.35–7.21 (5H,m); 7.01 (2H,d,J=8.52 Hz); 6.85 (2H,d,J=8.52 Hz); 4.89–4.79 (2H,m); 4.19 (2H, d,J=10.17 Hz); 3.91 (1H,q,J=6.6 Hz); 2.81–2.70 (2H,m); 2.49–2.43 (1H,m); 1.51 (1H,brs); 1.35 (12H,t,J=6.32 Hz); 1.29 (3H,d,J=6.59 Hz); 0.89 (3 H,d,J=6.33 Hz).

PROCEDURE 7

(R)-Diisopropyl4-(2-aminopropyl)phenoxymethylphosphonate

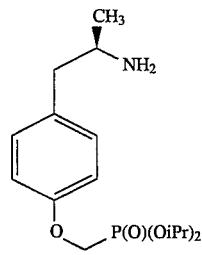

The title compound was obtained from (RR)-diisopropyl 4-[2-[2-(1-phenylethyl)amino] propyl]phenoxymethylphosphonate (2.48 g, 5.7 mMol), ammonium formate (2.5 g, 39 mMol) and 10% palladium charcoal (500 mg) by an analogous procedure to that described in Procedure 5.

$^1$H NMR δ(CDCl$_3$), 7.10 (2H,d,J=8.53 Hz); 6.89 (2H,d, J=8.80 Hz); 4.89–4.77 (2H,m); 4.20 (2H,d,J=10.17 Hz); 3.15–3.08 (1H,m); 2.65 (1H,dxd,J=5.5 and 13.47 Hz); 2.45 (1H,dxd,J=8.25 and 13.48 Hz); 1.46 (2H,brs); 1.36 (12H,t, J=6.32 Hz); 1.10 (3H,d,J=6.05 Hz).

PROCEDURE 8

(RR)-Di-n-butyl4-[2-[2-(1-phenylethyl)amino]propyl]phenoxymethylphosphonate

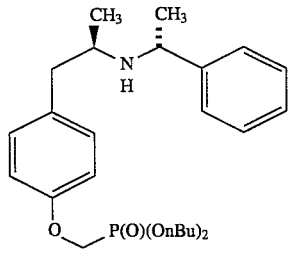

The title compound was obtained from di-n-butyl 4-(2-oxopropyl)phenoxymethylphosphonate (4.0 g, 10.5 mMol), R-α-methylbenzylamine (1.3 g, 10.5 mMol) and platinum IV oxide (30 mg) in ethanol (40 ml) by an analogous procedure to that described in Procedure 4 after chromatography over silica gel eluting with dichloromethane containing 3% methanol.

$^1$H NMR δ(CDCl$_3$), 7.35–7.26 (5H,m); 7.01 (2H,d,J=8.52 Hz); 6.85 (2H,d,J=8.79 Hz); 4.25 (2H,d,J=10.17 Hz); 4.19–4.05 (4H,m); 3.96–3.90 (1H, m); 2.81–2.70 (2H,m); 2.46–2.40 (1H, m); 1.70–1.62 (5H,m); 1.45–1.34 (4H,m);

1.29(3H,d,J=6.87 Hz); 0.92 (6H,t,J=7.42 Hz); 0.89 (3H,d, J=6.35 Hz).

PROCEDURE 9

(R)-Di-n-butyl 4-(2-aminopropyl)phenoxymethylphosphonate

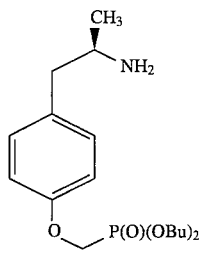

The title compound was obtained from (RR)-di-n-butyl4-[2-[2-(1-phenylethyl)amino] propyl]phenoxymethylphosphonate (0.8 g, 1.8 mMol), 10% palladium on charcoal (300 mg) and ammonium formate (0.5 g, 7.9 mMol) in methanol (30 ml) by an analogous procedure to that described in Procedure 5.

$^1$H NMR $\delta$(CDCl$_3$), 7.12 (2H,d,J=8.52 Hz); 6.89 (2H,d, J=8.80 Hz); 4.26 (2H,d,J=9.89 Hz); 4.16 (4H,q,J=6.59 Hz); 3.12 (1H,q,J=7.42 Hz); 2.66 (1H,dxd,J=5.22 and 13.19 Hz); 2.47 (1H,dxd, J=5.5 and 13.48 Hz); 1.74–1.60(6H,m); 1.48–1.40 (4H,m); 1.11 (3H,d,J=6.33 Hz); 0.93 (6H,t,J=7.42 Hz).

PROCEDURE 10

Diisopropyl4-formylphenoxymethylphosphonate

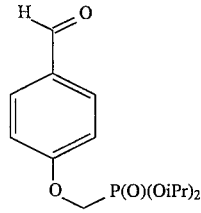

The title compound was obtained from diisopropylphosphite (12.9 ml, 77.5 mmol), 4-fluorobenzaldehyde (10 ml, 77.4 mMol) paraformaldehyde (2.4 g, 77.4 mMol) and sodium hydride (3.29 g of a 60% dispersion in oil) by analogous procedure to that described in Procedure 1. Chromatography over silica gel eluting with dichloromethane containing 3% methanol yielded a pale yellow oil.

$^1$H NMR $\delta$(CDCl$_3$), 9.95 (1H,s); 7.99 (2H,d,J=8.72 Hz); 7.22 (2H,d,J=8.79 Hz); 5.05–4.92 (2H, m); 4.44 (2H,d,J= 10.45 Hz); 1.51 (12H,t,J=6.05 Hz).

PROCEDURE 11

Di-n-butyl4-formylphenoxymethylphosphonate

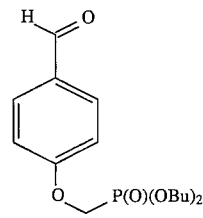

The title compound was obtained from di-n-butylphosphite (15.1 ml, 77.4 mMol), 4-fluorobenzaldehyde (2.4 g, 77.4 Mol), paraformaldehyde (2.4 g, 77.4 mMol) and sodium hydride (3.29 g of a 60% dispersion in oil) by an analogous procedure to that described in Procedure 1. Chromatography over silica gel eluting with dichloromethane containing 3% methanol yielded a pale yellow oil.

$^1$H NMR $\delta$(CDCl$_3$), 9.91 (1H,s); 7.84 (2H,d,J=8.52 Hz); 7.08 (2H,d,J=8.8 Hz); 4.36 (2 H,d,J=10.45 Hz); 4.17 (4H, q,J=6.6 Hz); 1.74–1.63 (4H,m); 1.48–1.34 (4H,m); 0.93 (6H,t,J= 7.43 Hz).

PROCEDURE 12

Diisopropyl 4-(2-nitropropenyl)phenoxymethylphosphonate

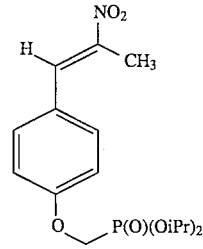

The title compound was obtained in a two step sequence. Initial treatment of diisopropyl 4-formylphenoxymethylphosphonate (6.7 g, 22.3 mMol) with n-butylamine (5 ml, 50 mMol) and benzene (70 ml) gave the N-butylimine. The intermediate thus generated was then reacted with nitroethane (10 ml) and acetic acid (20 ml) by an analogous procedure to that described in Procedure 2.

$^1$H NMR $\delta$(CDCl$_3$), 8.26 (1H,s); 7.11 (2H,d,J=8.5 Hz); 6.89 (2H,d,J=8.5 Hz); 4.95–4.70 (2H,m); 4.18 (2H,d,J=10.2 Hz); 2.10 (3H,s); 1.32 (6H,d,J=7.5 Hz).

PROCEDURE 13

Di-n-butyl 4-(2-nitropropenyl)phenoxymethylphosphonate

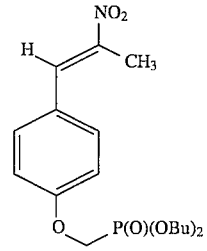

The title compound was obtained in a two step sequence. Initial treatment of di-n-butyl 4-formylphenoxymethylphosphonate (11.39 g, 32.4 mMol), n-butylamine (10 ml, 100 mMol) and benzene (70 ml) gave the N-butylimine. The intermediate thus generated was then reacted with nitroethane (10 ml) and acetic acid (20 ml) by an analogous procedure to that described in Procedure 2.

$^1$H NMR $\delta$(CDCl$_3$), 8.23 (1H,s); 7.60 (2H,d,J=8.5 Hz); 7.31 (2H,d,J=8.7 Hz); 4.5–4.1 (6H,m); 2.62 (3H,s,); 1.8–1.3 (8H,m); 1.11 (6H,t,J=7.5 Hz).

PROCEDURE 14

Diisopropyl 4-(2-oxopropyl)phenoxymethylphosphonate

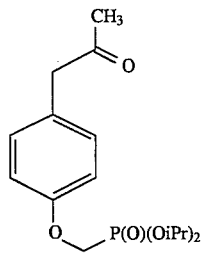

The title compound was obtained from diisopropyl 4-[2-nitropropenyl)phenoxymethylphosphonate (7.6 g, 21.5 mMol), iron powder (20 g), methanol (70 ml), water (20 ml) and acetic acid (30 ml) by an analogous procedure to that described in Procedure 3. Chromatography over silica gel eluting with hexane containing 30% ethyl acetate gave a pale yellow oil.

$^1$H NMR $\delta$(CDCl$_3$), 7.12 (2H,d,J=8.52 Hz); 6.93 (2H,d, J=8.52 Hz); 4.89–4.77 (2H,m); 4.20 (2H,d,J=10.45 Hz); 3.64 (2H, s); 2.14 (3H,s); 1.36 (12H,t,J=6.04 Hz).

PROCEDURE 15

Di-n-butyl 4-(2-oxopropyl)phenoxymethylphosphonate

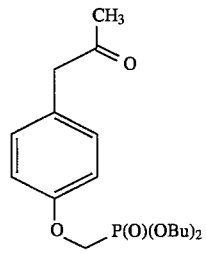

The title compound was obtained from di-n-butyl 4-(2-nitropropenyl)phenoxymethylphosphonate (12.1 g, 30 mMol), iron powder (15 g), methanol (70 ml), water (20 ml) and acetic acid (50 ml) by an analogous procedure to that described in Procedure 3. Chromatography over silica gel eluting with hexane containing 30% ethyl acetate gave a pale yellow oil.

$^1$NMR $\delta$(CDCl$_3$), 7.13 (2H,d,J=8.53 Hz); 6.92 (2H,d,J= 8.8 Hz); 4.27 (2H,d,=10.17 Hz); 4.21–4.12 (4H,m); 3.64 (2H,s); 2.15 (3H,s); 1.74–1.63 (4H,m); 1.48–1.37 (4H,m); 0.93 (6H,t,J=7.42 Hz).

PROCEDURE 16

(R)-Triethyl 4-[2-aminopropyl]phenoxyphosphonoacetate

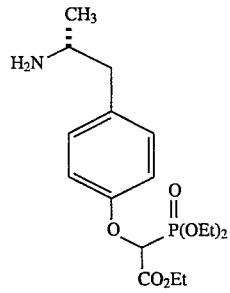

The title compound was obtained from (RR)-triethyl 4-[2-[2-(1-phenylethyl)amino] propyl]phenoxyphosphonoacetate (0.85 g, 1.78 mMol), 10% palladium on charcoal (500 mg) and ammonium formate (2 g) in methanol (20 ml) by an analogous procedure to that described in Procedure 5.

$^1$H NMR $\delta$(CDCl$_3$), 7.10 (2H,d,J=8.52 Hz); 6.86 (2H,d, J=8.79 Hz); 5.00 (1H,d,J=18.97 Hz); 4.35–4.24 (6H,m); 3.23–3.05 (1H,m); 2.71–2.65 (1H, m); 2.52–2.39 (1H,m); 1.74–1.38 ( 2H,br m); 1.37 (6H,t,J=7.15 Hz); 1.29 (3H,t,J= 7.14 Hz); 1.10 (3H,d,J=6.33 Hz).

PROCEDURE 17

(RR)-Triethyl 4-[2-[2-(1-phenylethyl)amino]propyl]phenoxyphosphonoacetate

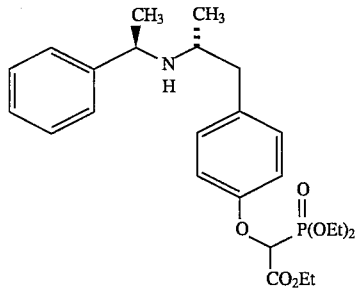

The title compound was obtained from triethyl 4-(2-oxopropyl)phenoxyphosphonoacetate (1.5 g, 4.0 mMol), (R)-$\alpha$-methylbenzylamine (0.48 g, 4.0 mMol) and platinum IV oxide (20 mg) in ethanol (25 ml) by an analogous procedure to that described in Procedure 4 after chromatography over silica gel eluting with dichloromethane containing 3% methanol.

$^1$H NMR $\delta$(CDCl$_3$), 7.33–7.23 (5H,m); 6.99 (2H,d,J=8.8 Hz); 6.82 (2H,d,J=8.52 Hz); 4.99 (1 H,d,J=18.97 Hz); 4.34–4.24 (6H,m); 3.90 (1H,q,J=6.87 Hz); 2.77–2.63 (2H, m); 2.47–2.40 ( 1H,m); 1.75–1.50 (1H,br m); 1.37 (6H,t,J= 7.15 Hz); 1.29 (3H,d,J=6.59 Hz); 1.28 (3H,t,J=7.15 Hz); 0.89 (3H,d,J=6.33 Hz).

PROCEDURE 18

Triethyl 4-(2-oxopropyl)phenoxyphosphonoacetate

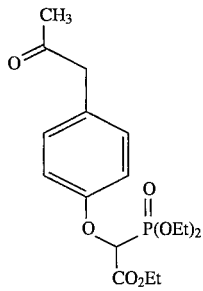

To a solution of methyl 4-[2-dioxalano-2-propyl]phenoxy] phosphonoacetate (2.27 g, 5.5 mMol) in acetone (20 ml) was added 2M aqueous hydrochloric acid (10 ml). After stirring at room temperature overnight the acetone was evaporated and the organic material extracted with diethyl ether (2×50 ml), The combined organic phases were dried and evaporated to yield the title compound as a yellow oil.

$^1$H NMR $\delta$(CDCl$_3$), 7.26 (2H,d,J=8.8 Hz); 7.02 (2H,d,J= 8.8 Hz); 5.15 (1H,d,J=18.97 Hz); 4.46–4.33 (6H,m); 3.77 (2H,s); 2.27 (3H,s); 1.51 (6H,t,J=6.87 Hz); 1.42 (3H,t,J= 7.15 Hz).

PROCEDURE 19

Triethyl 4-[2-[dioxalano-2-propyl]phenoxyphosphonoacetate

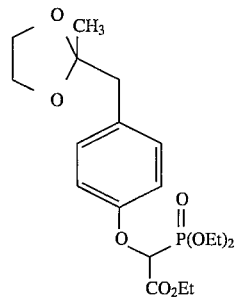

To a solution of 2-(4-hydroxyphenylmethyl)-2-methyldioxalane (2.65 g, 13.66 mMol) in benzene (50 ml) was added rhodium II acetate dimer (60 mg, 1 mole %). The solution was degassed under vacuum and then purged with nitrogen. The resultant green solution was heated to reflux and methyl diazo phosphonoacetate (3.75 g, 15.0 mMol) in benzene (10 ml) was added over a 1 h period. After 12 h the mixture was cooled and filtered, the benzene was evaporated to yield a dark yellow oil. Chromatography over silica gel eluting with hexane containing 35% diethyl ether gave the title compound as a pale green oil.

$^1$H NMR $\delta$(CDCl$_3$), 7.26 (2H,d,J=8.8 Hz); 6.91 (2H,d,J= 8.8 Hz); 5.07 (1H,d,J=18.97 Hz); 4.42–4.25 (6H, m); 3.98–3.89 (2H,m); 3.85–3.75 (2H,m); 2.95 (2H,s); 2.25 (3H, s,); 1.44 (6H,t,J=7.15 Hz); 1.35 (3H,t,J=7.15 Hz).

PROCEDURE 20

Ethyl 4-(2-oxopropyl)phenoxymethylphosphonic Acid

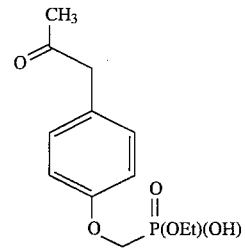

To suspension of ethyl 4-(2-dioxalano-2-propyl)phenoxymethylphosphonic acid (4.19 g, 13.0 mMol) in acetone (25 ml) was added 1M hydrochloric acid (10 ml). After stirring overnight the solvent was evaporated and the residue dissolved in a mixture of ethyl acetate and isopropanol (4:1). The solution was washed with brine, dried and evaporated to the product as a yellow oil.

H NMR $\delta$(D6 DMSO/D$_2$O), 7.11 (2H,d,J=8.52 Hz); 6.94 (2H,d,J=8.8 Hz); 4.19 (2H,d,J=9.89 Hz); 4.16–4.02 (2H,m); 3.67 (2H,s); 2.10 (3H,s); 1.26 (3H,t,J=6.88 Hz).

PROCEDURE 21

Ethyl 4-[2-dioxalano-2-propyl]phenoxymethylphosphonic Acid

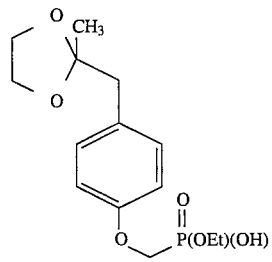

A solution of diethyl 4-[2-dioxalano-2-propyl]phenoxymethylphosphonate (5 g, 14.5 mMol) in dioxane (25 ml) was treated with 1M lithium hydroxide (20 ml). After stirring overnight the dioxane was evaporated and the aqueous residue adjusted to pH 7 by addition of 2M hydrochloric acid. Evaporation and drying under vaccum yielded the title compound as a white solid contaminated with lithium chloride.

¹H NMR δ(D6 DMSO), 7.19 (2H,d,J=8.52 Hz); 6.90 (2H,d,=8.52 Hz); 4.0–3.8 (8H,m); 2.84 (2H,s); 1.24 (3H,s); 1.19 (3H,t,J=6.88 Hz).

PROCEDURE 22

Diethyl 4-[2-dioxalano-2-propyl]phenoxymethylphosphonate

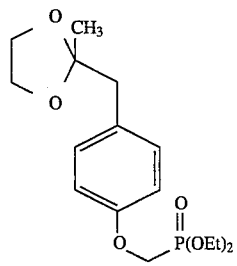

A mixture of diethyl 4-(2-oxopropyl)phenoxymethylphosphonate (10 g, 33.3 mMol), 1,2-ethanediol(1.84 ml, 33.3 mMol) and 4-toluenesulphonic acid monohydrate (0.5 g) in benzene (75 ml) was heated under reflux with removal of water. After 12 h a further equivalent of 1,2-ethanediol was added and heating continued for 10 h. The reaction mixture was cooled and washed with sodium bicarbonate solution. The organic layer was washed with water, dried and evaporated to yield the title compound as straw coloured oil.

¹H NMR δ(CDCl₃), 7.20 (2H,d,J=8.53 Hz); 6.88 (2H,d, J=8.8 Hz); 4.37–4.18 (6H,m); 3.93–3.84 (2H,m); 3.80–3.71 (2H,m); 2.86 (2H,s); 1.37 (6H,t,J=7.14 Hz); 1.29 (3H,s).

EXAMPLE 1

(RR,SS)-Diethyl 4-[2-[2-(3-chlorophenyl)-2-hydroxyethylamino]propyl]phenoxymethylphosphonate Hydrochloride

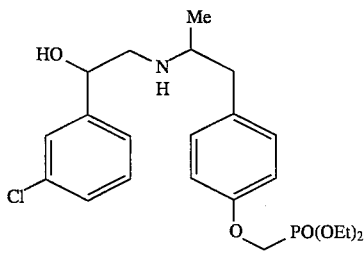

A mixture of 1-(3-chlorophenyl)-2-aminoethanol (0.86 g, 5 mMol) and diethyl 4-( 2-oxopropyl)phenoxymethylphosphonate (1.5 g, 5 mMol) dissolved in methanol (25 ml) was treated with platinum IV oxide (50 mg) and stirred under an atmosphere of hydrogen for 12 h. The mixture was filtered through celite and the methanol evaporated. The crude product was chromatographed on silica gel eluting with 0–2% methanol in dichloromethane to yield the secondary amine as a viscous oil. This was dissolved in ethyl acetate and treated with ethereal hydrogen chloride, cooled to −15° C. and fractional crystallisation gave the product as the (RR,SS) diastereomer as a white solid, after filtering and drying under vacuum (m.p. 84°–86° C.).

¹H-nmr δ(D6-DMSO), 9.3–9.0 (1H, br s, exchanges with D₂O); 8.8–8.5 (1H, br s, exchanges with D₂O); 7.5–7.3 (4H, m); 7.17 (2H, d, J=8.52 Hz); 7.00 (2H, d, J=8.52 Hz); 6.63 (1H, d, J= 3.77 Hz; exchanges with D₂O); 4.39 (2H, d, J=9.62); 4.2–4.0 (4H, m); 3.5–3.0 (4H, complex multiplet); 2.61 (1H, t, J=10.45 Hz); 1.25 (6H, t, J=7.15 Hz); 1.10 (3H, d, J= 6.32 Hz).

EXAMPLE 2

(RR,SS)-Sodium Ethyl 4-[2-[2-(3-chlorophenyl)-2-hydroxyethylamino]propyl]phenoxymethylphosphonate

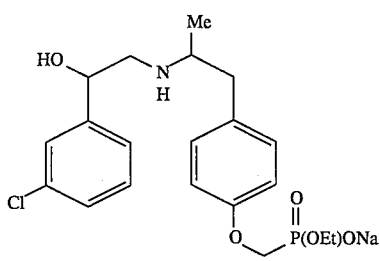

(RR,SS)-Diethyl 4-[2-[2-(3-chlorophenyl )-2-hydroxyethylamino]propyl]phenoxymethylphosphonate hydrochloride (106 mg, 0.22 mMol) was suspended in dioxane (2 ml) and treated with 2.5M aqueous sodium hydroxide solution (2.0 ml). After stirring at room temperature for 24 h the dioxane was evaporated and the residual solution adjusted to pH9. Chromatography on C18 reverse phase silica eluting with water then 25–50% isopropanol in water, gave the title compound as a white solid, m.p. 122°–5° C.

¹H-nmr δ(CD₃OD), 7.45 (1H, s); 7.4–7.3 (3H, m); 7.13 (2H, d, J=8.6 Hz); 6.93 (2H, d, J=8.7 Hz); 4.90 (1H, dxt, J=9.0 Hz); 4.1–4.0 (4H, ml; 3.3–3.2 (1H, m); 3.2–2.9 (3H, m); 2.68 (1H, dxd, J=13.4 Hz); 1.25 (3H, t, J=7.1 Hz); 1.19 (3H, d, J=6.5 Hz).

EXAMPLE 3

(RR)-Diethyl 4-[2-[2-(3-chlorophenyl)-2-hydroxyethylamino]propylphenoxymethylphosphonate

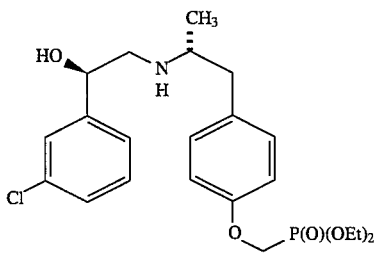

A mixture of (R)-diethyl-4-(2-aminopropyl)phenoxymethylphosphonate (388 mg, 1.29 mMol) and trimethylsilyl acetamide (168 mg, 1.29 mMol) in dimethyl sulfoxide (2.5 ml) was stirred at room temperature. After 0.5 h the mixture was treated with (R)-3-chlorophenyloxirane (200 mg, 1.29 mMol) and heated at 75° C. under nitrogen for 50 h. The resultant solution was cooled and partitioned between water (10 ml) and ethyl acetate (20 ml). After drying and evaporation the organic layer gave a brown oil, chromatography of which, over silica gel eluting with dichloromethane containing 4% methanol, gave the title compound as a colourless oil.

¹H NMR δ(CDCl₃), 7.34 (1H,s); 7.26–7.17 (3H,m); 7.09 (2H,d,J=8.52 Hz); 6.89 (2H,d,J=8.52 Hz); 4.55 (1H,dxd,J= 3.85 and 8.80 Hz); 4.30–4.19 (6H, m); 2.95–2.79 (2H,m); 2.75–2.57 (5H,m); 1.36 (6H,t,J=7.15 Hz); 1.06 (3H, d,J= 6.05 Hz).

EXAMPLE 4

(RR)-Ethyl Sodium 4-[2-[2-(3-chlorophenyl)-2-hydroxyethylamino]propyl]phenoxymethylphosphonate

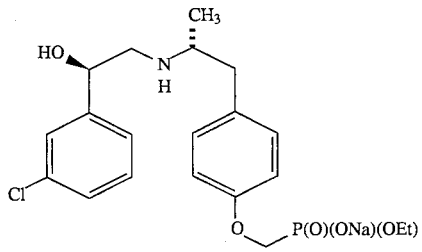

The title compound was obtained from (RR)-diethyl 4-[2-[2-(3-chlorophenyl)-2-hydroxyethylamino] propyl]phenoxymethylphosphonate (110 mg, 0.24 mMol), 2M aqueous sodium hydroxide (2 ml) and dioxane (4 ml) by an analogous procedure to that described in Example 2. After chromatography over $C_{18}$ reverse phase silica eluting with water/isopropanol (3:1) a white powder was obtained, mp>290° C.

$^1$H NMR δ(CD$_3$OD), 7.35–7.30 (3H,m); 7.26 (1H,s); 7.00 (2H,d,J=8.59 Hz); 6.87 (2H,d,J=8.64 Hz); 4.67 (1H,t,J=6.83 Hz); 4.15–4.00 (4H,m); 2.98 (1H,dxd,J=7.03 and 11.70 Hz); 2.90–2.80 (1H,m); 2.70–2.60 (2H,m); 2.50 (1H,dxd,J=8.28 and 13.51 Hz); 1.28 (3H,t,J= 7.08 Hz); 1.10 (3H,d,J=6.25 Hz).

EXAMPLE 5

(RR)-Diisopropyl 4-[2-[2-(3-chlorophenyl)-2-hydroxyethylamino]propyl]phenoxymethylphosphonate

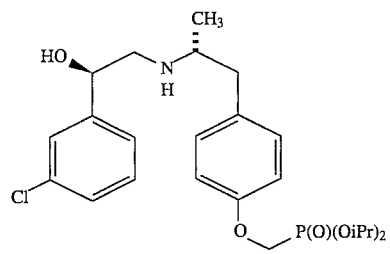

The title compound was obtained from (R)-diisopropyl 4-[2-aminopropyl]phenoxymethylphosphonate (600 mg, 1.82 mMol), N-trimethylsilylacetamide (267 mg, 1.87 mMol), (R)-3-chlorophenyloxirane (290 mg, 1.87 mMol) and dimethyl sulphoxide (2 ml) by analogous procedure to that described in Example 3. Chromatography over silica gel eluting with dichloromethane containing 3% methanol yielded a colourless oil.

$^1$H NMR δ(CDCl$_3$), 7.34 (1H,s); 7.26–7.21 (3H,m); 7.09 (2H,d,J=8.52 Hz); 6.89 (2H,d,J=8.53 Hz 4.86–4.76 (3H,m); 4.58 (1H,dxd,J=3.30 and 8.80 Hz); 4.20 (2H,d,J=10.17 Hz); 2.92–2.86 (2H,m); 2.70–2.62 (3H,m); 1.36 (12H,t,J=6.05 Hz); 1.08 (3H,d,J=6.32 Hz).

EXAMPLE 6

(RR)-Isopropyl Sodium 4-[2-[2-(3-chlorophenyl)-2-hydroxyethylamino]propyl]phenoxymethylphosphonate

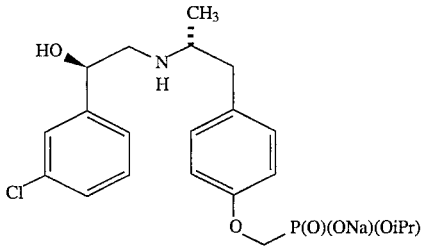

The title compound was obtained from (RR)-diisopropyl 4-[2-[2-(3-chlorophenyl)-2-hydroxyethylamino] propyl] phenoxymethylphosphonate (350 mg, 0.72 mMol), 2M aqueous sodium hydroxide (2 ml) and dioxane (2 ml) by an analogous procedure to that described Example 2. Chromatography over $C_{18}$ reverse phase silica eluting with water containing 30% isopropanol gave a white solid, mp 299°–301° C.

$^1$H NMR δ(CD$_3$OD), 7.35–7.26 (3H,m); 7.21–7.18 (1H, m); 7.03 (2H,J=8.6 Hz); 6.88 (2H,J=8.6 Hz); 4.30–4.24 (1H,m); 4.13–4.06 (1H,m); 4.04 (2H, d,J=10.1 Hz); 2.95–2.80 (3H,m); 2.71–2.53 (2H,m); 1.26 (6H,t,J=6.2 Hz); 1.08 (3H,d,J=6.2 Hz).

EXAMPLE 7

(RR)-Di-n-butyl 4-[2-[2-(3-chlorophenyl)-2-hydroxyethylamino]propyl]phenoxymethylphosphonate

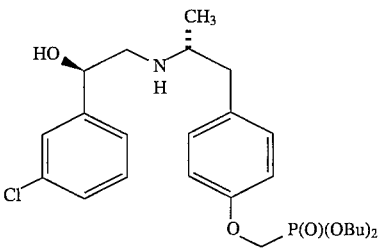

The title compound was obtained from (R)-di-n-butyl 4-(2-aminopropyl)phenoxymethylphosphonate (560 mg, 1.64 mMol), N-trimethylsilylacetamide (240 mg, 1.82 mMol) and (R)-3-chlorophenyloxirane (262 mg, 1.69 mMol) in dimethyl sulfoxide (5 ml) by an analogous procedure to that described in Example 3. Chromatography over silica gel eluting with dichloromethane containing 3% methanol yielded a pale yellow oil.

$^1$H NMR δ(CDCl$_3$), 7.34 (1H,s); 7.26–7.20 (3H,m); 7.08 (2H,d,J=8.52 Hz); 6.89 (2H,d,J=8.52 Hz); 4.59–4.51 (2H, m); 4.26 (2H, d,J=11.54 Hz); 4.19–4.12 (4H,m); 2.90–2.85 (1H,m); 2.65–2.61 (2H,m); 2.25–2.00 (2H,brm); 1.71–1.63 (3H,m); 1.46–1.37 (4H,m); 1.08 (3H,d,J=6.32 Hz); 0.93 (6H,t,J=7.42 Hz).

EXAMPLE 8

(RR)-n-Butyl Sodium 4-[2-[2-(3-chlorophenyl)-2-hydroxyethylamino]propyl]phenoxymethylphosphonate

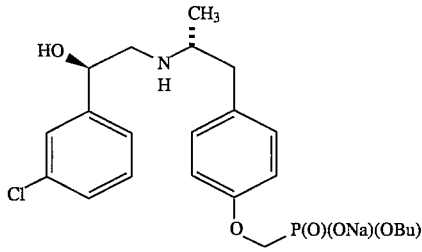

The title compound was obtained from (RR)-di-n-butyl 4-[2-[2-(3-chlorophenyl)-2-hydroxyethylamino] propyl] phenoxymethylphosphonate (240 mg, 0.46 mMol), 2M aqueous sodium hydroxide (2 ml) and dioxane (2 ml) by an analogous procedure to that described in Example 2. After chromatography over $C_{18}$ reverse phase silica gel eluting with water containing 20% isopropanol a white powder was obtained, mp>300° C.

$^1$H NMR $\delta$(CD$_3$OD), 7.32–7.25 (3H,m); 7.16–7.13 (1H, m); 6.97 (2H,d,J=8.63 Hz); 6.85 (2H,d,J= 8.67 Hz); 4.65 (1H,t,J=6.85 Hz); 4.08 (2H,d,J=9.86 Hz); 4.01–3.94 (2H,m); 2.98 (1 H,dxd,J=6.72 and 11.53 Hz); 2.88–2.70 (1H,m); 2.67–2.52 (1H,m); 2.45 (2H,dxd,J=8.52 and 13.59 Hz); 1.64–1.55 (2H,m); 1.43–1.33 (2H,m); 1.08 (3H,d,J=6.12 Hz); 0.89 (3H,t,J=7.32 Hz).

EXAMPLE 9

(RR)-Disodium 4-[2-[2-(3-Chlorophenyl)-2-hydroxyethylamino]propyl]phenoxymethylphosphonate

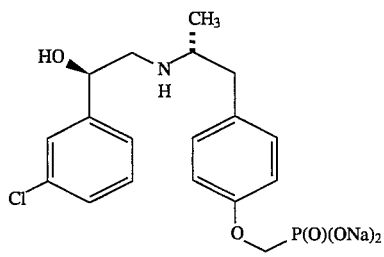

A mixture (RR) of diisopropyl 4-[2-[2-(3-chlorophenyl)-2-hydroxyethylaminopropylmethylphosphonate (100 mg, 0.2 mMol) and 6M aqueous hydrochloric acid (2.5 ml) was heated at 100° C. under an atmosphere of nitrogen for 12 h. After cooling and evaporation of the solvent the resultant green gum was treated with aqueous saturated sodium bicarbonate (1 ml) and the residue chromatographed over $C_{18}$ reverse phase silica to yield the title compound as a white crytstalline powder, top>300° C.

$^1$H NMR $\delta$D$_2$O/DCl, 7.36–7.31 (3H,m); 7.27–7.21 (1H, m); 7.18 (2H,d,J=8.68 Hz); 6.98 (2H,d,J= 8.69 Hz), 4.95 (1H,t,J=6.63 Hz); 4.22 (2H,d,J=9.92 Hz); 3.59–3.53 (1H,m); 3.32–3.13 (2H,m); 3.02–2.96 (1H,m); 2.84–2.78 (1H,m); 1.23 (3H,d,J=6.6 Hz).

EXAMPLE 10

(RR) Dilithium ethyl 4-[2-[2-(3-chlorophenyl)-2-hydroxyethylamino]propyl]phenoxyphosphonoacetate

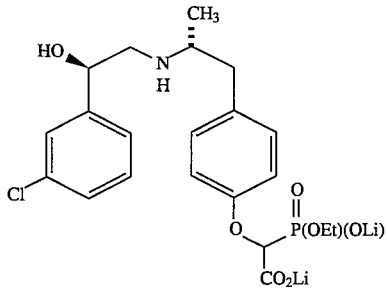

The title compound was obtained from (RR)-triethyl 4-[2-[2-(3-chlorophenyl)-2-hydroxyethylamino] propyl]phenoxyphosphonoacetate (174 mg, 0.37 mMol), 1M lithium hydroxide (2 ml) and dioxane (3 ml) by an analogous procedure to that described in Example 2. After chromatography over $C_{18}$ reverse phase silica eluting with water/isopropanol (9:1) a white powder was obtained, mp>300° C.

$^1$H NMR $\delta$(CD$_3$OD/D$_2$O), 7.43 (1H,s); 7.39–7.32 (2H, m); 7.32–7.29 (1H,m); 7.14 (2H,dxd,J=8.36 and 7.2 Hz); 6.92 (2H,dxd,J=8.36 and 7.2 Hz); 4.90–4.88 (1H,m); 4.68 (1H,d,J=18.1 Hz); 4.08–4.01 (2H,m); 3.20–3.00 (2H,m); 2.95–2.80 (1H,m); 2.80–2.70 (1H,m); 1.24 (3H,t,J=5.8 Hz); 1.18 (3H,d,J=12 Hz).

EXAMPLE 11

(RR) Triethyl 4-[2-[2-(3-chlorophenyl)-2-hydroxyethylamino]propyl]phenoxyphosphonoacetate

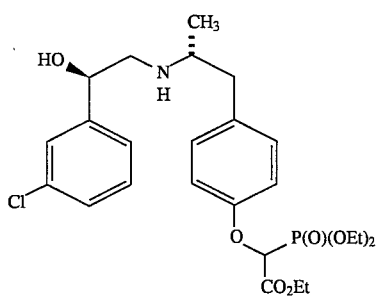

The title compound was obtained from (R) triethyl 4-[2-aminopropyl]phenoxyphosphonoacetate (0.56 g, 1.5 mMol), N-trimethylsilylacetamide (200 mg, 1.5 mMol), (R)-3-chlorophenyloxirane (230 mg, 1.5 mMol) and dimethyl sulphoxide (4 ml) by an analogous procedure to that described in Example 3. Chromatography over silica gel eluding with dichloromethane containing 3% methanol yielded a pale yellow oil.

$^1$H NMR $\delta$(CDCl$_3$/D$_2$O), 7.35 (1H,s); 7.3–7.1 (3H,m); 7.06 (2H,d,J=8.52 Hz); 6.86 (2H,d,J=8.52 Hz); 5.04 (1H,d, J=18.9 Hz); 4.65 (1H,m); 4.0–4.1 (6H,m); 3.0–2.8 (1H,m); 2.7–2.6 (3H,m); 2.0–1.9 (1H,m); 1.37 (6H,t,J=7.15 Hz); 1.29 (3H,t,J=7.15 Hz); 1.08 (3H,d,J= 6.32).

EXAMPLE 12

(RR,RS) Ethyl 4-[2-[2-(3,4-dihydroxyphenyl)hydroxyethyl-amino]propyl]phenoxymethylphosphonic Acid

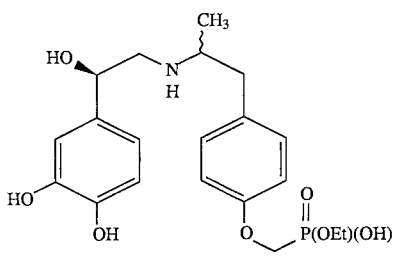

A mixture of ethyl 4-(2-oxopropyl)phenoxymethyl phosphonic acid (0.8 g, 2.96 mMol) and (R)-noradrenaline (0.5 g, 2.96 mMol) in methanol (50 ml) was stirred at room temperature for 0.5 h. Palladium on charcoal (10%, 0.3 g) was then added and the resultant mixture hydrogenated at 50 psi, 50° C. for 20 h. After filtration and evaporation of the solvent the crude product was chromatographed over $C_{18}$ reverse phase silica eluting with water containing isopropranol 20% gave a pale yellow gum freeze drying of which yielded the title compound as a white fluffy solid, mp 170°–3° C.

$^1$NMR δ(D$_2$O), 7.28–7.10 (2H,m); 7.09–6.93 (2H,m); 6.91–6.81 (2H,m); 6.82–6.74 (1H,m); 4.18 (2H,d,J=9.5 Hz); 4.09–3.95 (2H,m); 3.60–3.48 (1H,m); 3.40–3.15 (2H,m); 3.00–2.80 (3H,m); 1.30 (3H,d,J=6.2 Hz); 1.26 (3H,t,J=6.8 Hz).

PHARMACOLOGICAL DATA

Lipolysis

Rat white adipocytes were prepared by collagenase digestion as described by Rodbell (1964) with the modification of Honnor et al. (1985), in that adenosine (200 nM) was included in the preparation to inhibit basal lipolysis.

Lipolysis stimulated by β-agonists was measured over 30 minutes in medium where the adenosine concentration was controlled; the medium included (–)-N$^6$-(2-phenylisopropyl)adenosine (100 nM)+deaminase as decribed by Honnor et al. (1985). The incubation was stopped by addition of trichloracetic acid (0.2 ml of 10% w/v) to 1 ml of cells. Glycerol was measured by the fluorimetric method of Boobis and Maugham (1983).

References

1. Rodbell M. (1964) J. Biol. Chem. 239, 375–380
2. Honnor R. C., Dhellon G. S. and Londos C. (1985) J. Biol. Chem. 260, 15122–15129
3. Boobis L. H. and Maugham R. J. (1983) Clinica Chemica Acta 132, 173–179.

Phosphonic acid derivative of Example 2, EC$_{50}$=77 nM (Intrinsic Activity =0.95).

Agonist Activity at Rat β$_1$ and β$_2$ Adrenoceptors In Vitro

β$_1$-Adrenoceptor Agonism

Female Sprague-Dawley rats (150–250 g) were killed by a blow to the head and exsanguinated. Spontaneously beating right atria were removed by the method of Broadley and Lumley (1977) and mounted on a glass tissue holder. Each tissue was placed in 30 ml organ baths at 37° C. containing Kreb's-Henseleit solution. Each atrium was attached to an isometric transducer by cotton and placed under an initial resting tension of 1 g. Rate recordings from the spontaneous beating atria were obtained from the tension signal using a Lectromed Type 4522 ratemeter. All traces were recorded on a Lectromed M4 chart recorder. β-adrenoceptor agonists were then added to the Krebs medium in a cumulative fashion and the results expressed as a percentage increase in atrial rate.

β$_2$-Adrenoceptor Agonism

Rat uterine horns were removed and bisected longitudinally. Each tissue was tied to a glass tissue holder and placed in Krebs-Henseleit solution in a 30 ml organ bath as before. Tissues were placed under a resting tension of 1 g and allowed to equilibrate. Each uterine strip was pre-contracted by the addition of 40 mM K$^+$ to the bath to produced a steady tonic contraction. β-agonists were then added to the bath in a cumulative manner and results were expressed as percentage inhibition of contraction.

Agonist EC$_{50}$ (atria) and IC$_{50}$ (uteri) were calculated as the concentration of agonist producing 50% of their maximum increase in atrial rate or uterine relaxation. Relative intrinsic activity expressed as the maximal responses to test agonists relative to isoprenaline (=1.0) in both atria and uteri.

References

K. J. Broadley & P. Lumley (1977) Br. J. Pharmacol. 59. 51

|  | Ki(nM) | |
| --- | --- | --- |
|  | β$_1$ | β$_2$ |
| Example 2 | 37580 | 10000 |

We claim:
1. A compound of formula (I):

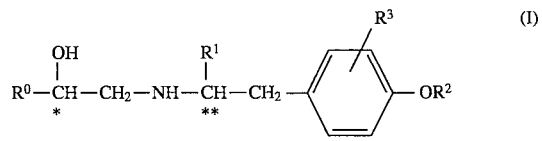

or a pharmaceutically acceptable salt, ester or amide thereof thereof, or a pharmaceutically acceptable solvate thereof, wherein, R$^o$ represents a substituted or unsubstituted aryl group;

R$^1$ represents hydrogen or an alkyl group;

R$^2$ represents a moiety of formula (a):

wherein

R$^4$ and R$^5$ each independently represent hydrogen, alkyl, hydroxyalkyl, cycloalkyl or R$^4$ together with R$^5$ represents (CH$_2$)$_n$ wherein n is 2, 3 or 4;

T represents hydrogen, nitrile or a group —CO.R$^s$ wherein R$^s$ represents hydroxy, alkoxy or a group NR'R" wherein R' and R" independently represent hydrogen, alkyl or R' and R" together with the nitrogen to which they are attached represent a saturated heterocyclic group; and $R^3$ represents hydrogen, halogen, alkyl or alkoxy.

2. A compound according to claim 1, wherein $R^o$ represents a phenyl group optionally substituted with halogen or a hydroxy group.

3. A compound according to claim 1, wherein $R^1$ is a methyl group.

4. A compound according to claim 1, wherein $R^4$ is alkyl and $R^5$ is hydrogen.

5. A compound according to claim 1, wherein T represents hydrogen.

6. A compound according to claim 1, wherein $R^3$ represents hydrogen.

7. A compound according to claim 2, wherein $R^1$ is methyl.

8. A compound according to claim 7 wherein $R^4$ is alkyl and $R^5$ is hydrogen.

9. A compound according to claim 8 wherein T is hydrogen.

10. A compound according to claim 9 wherein $R^3$ is hydrogen.

11. A compound selected from the group consisting of:

(RR,SS)-Diethyl 4-[2-[2-(3-chlorophenyl)-2-hydroxyethylamino]propyl]phenoxymethylphosphonate;

(RR,SS)-Sodium ethyl 4-[2-[2-(3-chlorophenyl)-2-hydroxyethylamino]propyl]phenoxymethylphosphonate;

(RR)-Diethyl 4-[2-[2-(3-chlorophenyl)-2-hydroxyethylamino]propyl]phenoxymethyl phosphonate;

(RR)-Ethyl sodium 4-[2-[2-(3-chlorophenyl)-2-hydroxyethylamino]propyl]phenoxymethyl phosphonate;

(RR-Diisopropyl 4-[2-[2-(3-chlorophenyl)-2-hydroxyethylamino]propyl]phenoxymethylphosphonate;

(RR-Isopropyl sodium 4-[2-[2-(3-chlorophenyl)-2-hydroxyethylamino]propyl]phenoxymethylphosphonate;

(RR)-Di-n-butyl 4-[2-[2-(3-chlorophenyl)-2-hydroxyethylamino]propyl]phenoxymethylphosphonate;

(RR)-n-Butyl sodium 4-[2-[2-(3-chlorophenyl)-2-hydroxyethylamino]propyl]phenoxymethylphosphonate;

(RR)-Disodium 4-[2-[2-(3-chlorophenyl)-2-hydroxyethylamino]propyl]phenoxymethylphosphonate;

(RR)-Dilithium ethyl 4-[2-[2-(3-chlorophenyl)-2-hydroxyethylamino]propyl] phenoxymethylphosphonoacetate;

(RR)-Triethyl 4-[2-[2-(3-chlorophenyl)-2-hydroxyethylamino]propyl]phenoxymethyl phosphonoacetate; and (RR)-Ethyl 4-[2-[2-(3-chlorophenyl)-2-hydroxyethylamino]propyl]phenoxymethyl phosphononic acid;

and pharmaceutically acceptable salts, esters, amides and solvates thereof.

12. A pharmaceutical composition comprising a compound according to claim 11 and a pharmaceutically acceptable carrier.

13. A pharmaceutical composition comprising a compound according to claim 1 and a pharmaceutically acceptable carrier therefor.

14. A method for treating hyperglycaemia, obesity, atherosclerosis, hyperinsulinaemia or irritable bowel syndrome in a human or non-human mammal, which comprises administering an effective, non-toxic, amount of a compound according to claim 1, to the human or non-human mammal in need thereof.

15. A method for increasing weight gain or improving the feed utilisation efficiency or increasing lean body mass and/or decreasing birth mortality rate and increasing post/natal survival rate; of livestock, which method comprises the administration to livestock of an effective non-toxic amount of a compound of formula (I), as defined in claim 1, or a veterinarily acceptable salt, ester or amide thereof; or a veterinarily acceptable solvate thereof.

16. A veterinarily acceptable premix formulation comprising a compound of formula (I), as defined in claim 1, or a veterinarily acceptable salt, ester or amide thereof; or a veterinarily acceptable solvate thereof, in association with a veterinarily acceptable carrier therefore.

* * * * *